United States Patent [19]

Lentz et al.

[11] 4,323,358

[45] Apr. 6, 1982

[54] METHOD FOR INHIBITING MINERALIZATION OF NATURAL TISSUE DURING IMPLANTATION

[75] Inventors: David J. Lentz, Mission Viejo; Elisabeth M. Pollock, Yorba Linda, both of Calif.

[73] Assignee: Vascor, Inc., Anaheim, Calif.

[21] Appl. No.: 259,762

[22] Filed: Apr. 30, 1981

[51] Int. Cl.$^3$ .............................................. A61F 1/22
[52] U.S. Cl. ......................................... 8/94.11; 3/1.4; 3/1.5
[58] Field of Search ................... 8/94.11; 3/1, 1.4, 1.5

[56] References Cited

U.S. PATENT DOCUMENTS 3,966,401 6/1976 Hancock et al. ...................... 8/94.11
4,050,893 9/1977 Hancock et al. ...................... 8/94.11

FOREIGN PATENT DOCUMENTS 559701 7/1977 U.S.S.R. ............................. 8/94.11

OTHER PUBLICATIONS

Miller, Zelma B., et al.: "The Effect of Dyes on the Calcification of Hypertrophic Rachitic Cartilage In Vitro", J. Exp. Med. 95, 497-508 (1952).

Sobel, Albert Edward et al.: "Calcification XIV. Investigation of the Role of Chondroitin Sulfate in the Calcifying Mechanism", Proc. Soc. Exp. Biol. Med. 87, 7-13 (1954).

Urist, Marshall R., et al.: "Effects of Various Blocking Reagents Upon Local Mechanism of Calcification", Arch. Pathol. 81, 325-342 (1966).

*Primary Examiner*—Maria Parrish Tungol
*Attorney, Agent, or Firm*—Wayne R. Eberhardt

[57] ABSTRACT

Natural tissues fixed with a tanning solution such as glutaraldehyde and intended for implantation in humans, e.g., porcine heart valve prosthetic devices, are treated with a solution of a water soluble salt of a sulfated higher aliphatic alcohol such as sodium dodecyl sulfate to inhibit mineralization, particularly calcification, of the tissue after implantation.

19 Claims, No Drawings

METHOD FOR INHIBITING MINERALIZATION OF NATURAL TISSUE DURING IMPLANTATION

BACKGROUND OF THE INVENTION

This invention relates to the preparation of natural tissue for implantation, and more particularly, to the treatment of fixed tissue to inhibit mineralization, particularly calcification, upon implantation.

Animal tissues have in recent years found wide acceptance in the preparation of various prosthetic devices for use in humans. Most notable of these is the use of porcine heart valves to replace defective mitral, tricuspid and aortic valves in humans. Also of interest is the preparation of arteries, veins and human umbilical cords for use as arterial grafts and other tubular duct replacement in humans.

Porcine heart valves have been in use for several years with generally good results. The preparation of such valves for implantation is described in the literature and in the patent art as, for example, in U.S. Pat. Nos. 3,966,401 and 4,050,893. Briefly, the valve is excised from the donor heart, trimmed and cleaned, and fixed by immersion in a tanning fluid such as a 0.2% glutaraldehyde solution. After several hours of treatment, the fixed valve is removed from the glutaraldehyde, rinsed, mounted on a stent, and stored in a glutaraldehyde solution until ready for use.

One problem which has been associated with the porcine heart valve in some individuals is calcification of the valve leaflets after an extended period of time resulting in reduced flexibility and eventual loss of efficiency in the operation of the valve. Significant calcification is readily visible in an X-ray of the affected valve.

It is accordingly an object of the present invention to provide a method to inhibit mineralization, and particularly calcification, of fixed natural tissue upon implantation.

It is a further object of this invention to provide a method for treatment of fixed porcine heart valve tissue to inhibit mineralization when used as a prosthetic valve replacement in humans.

These and other objects of the present invention will be apparent from the ensuing description and claims.

As used herein, the term "fixed" or "fixed tissue" refers to tissue which has been treated with a tanning solution such as 4% formaldehyde or 0.2% glutaraldehyde for a period of time and under conditions conventionally used to prepare natural tissue for implantation. The tanning process does not form any part of the present invention.

SUMMARY OF INVENTION

Natural tissue such as porcine heart valves which have been fixed for implantation in accordance with conventional procedures are treated prior to implantation with a solution of a water soluble salt of a sulfated higher aliphatic alcohol containing from 7 to 18 carbon atoms such as sodium dodecyl sulfate (SDS). The treatment may be effected in a 1% solution of SDS at ambient temperatures and for a period of about 24 hours. The treated tissue is removed from the SDS solution, rinsed, and returned to storage in sterile gluteraldehyde until needed for implantation.

DESCRIPTION OF PREFERRED EMBODIMENTS

In the method of the present invention, fixed natural tissue is treated with an aqueous solution of a water soluble salt of a sulfated higher aliphatic alcohol containing from 7 to 18 carbon atoms. The alkyl unit may be straight chain or branched, and preferred alkyl sulfates include the water soluble salts of lauryl sulfate, myristyl sulfate, cetyl sulfate, steryl sulfate, and oleyl sulfate. Mixtures of two or more alkyl sulfates may also be used if desired. The salt of the alkyl sulfate is preferably soluble in water at room temperature to a concentration of at least about 2%, and preferably at least 5% by weight. Suitable salts include the sodium, potassium and ammonium salts of $C_{7-18}$ alkyl sulfate, and amine salts such as triethylamine-lauryl sulfate. The sodium salt of lauryl (dodecyl) sulfate is most particularly preferred and its use is illustrated in the following detailed example.

An SDS treatment solution (1%) was prepared by dissolving 10 g of SDS and 1.4 g of N-2-hydroxyethyl-piperazine-N'-2-ethanesulfonic acid (HEPES) in one liter of distilled water, and the pH of the solution was adjusted to 7.4 with 1.0 N sodium hydroxide.

Fifty pieces of fixed porcine valve cusp tissue weighing from about 0.4 to 0.6 mg each were rinsed in saline solution to remove the glutaraldehyde, then placed in 50 ml of the SDS treatment solution at ambient temperature of 20°–25° C. The solution containing the tissue pieces was stirred continuously on a magnetic stirrer. The glutaraldehyde solution was changed after 8 hours, and the treatment was continued for a total of 24 hours.

After the SDS treatment, the tissue pieces were rinsed in 0.2% glutaraldehyde solution, resterilized by immersion for 24 hours in a solution of 1% glutaraldehyde/20% isopropyl alcohol, and returned to sterile 0.2% glutaraldehyde solution to await implantation.

The effectiveness of the SDS treatment in retarding calcification of the fixed tissue was determined by animal implant studies according to the following procedure.

Male Sprague-Dawley rats weighing 180–200 g were anesthetized and prepared for abdominal surgery under sterile conditions. The abdominal area was shaved, disinfected, and a lengthwise midline skin incision approximately 4 cm long was made in the ventral surface. The skin was separated from the underlying muscle, and three small pouches were formed in the muscle on either side of the midline incision by a small incision followed by blunt dissection of the abdominal muscle wall. One piece of SDS-treated tissue, rinsed in sterile saline to remove the glutaraldehyde, was inserted in each muscle pouch. The skin incision was closed and the animal returned to its cage. Implantations were made in 10 rats for a total of 60 pieces of SDS-treated tissue. A control group of 10 rats were implanted under identical conditions with a total of 60 pieces of fixed porcine valve cusp tissue not subjected to the SDS treatment.

Five rats from the control group and five from the SDS test group were sacrificed after four weeks and the implanted tissue examined for calcification by X-ray and hydrochloric acid extraction. The entire abdominal wall with implants in situ was excised and X-rayed. The implants were then removed and two set aside for histological examination while the remaining four were dissected free of surrounding tissue and extracted individually in 5 ml of 0.6 N HCl at 70° C. for 96 hours. The extract solution was then assayed for calcium by atomic absorption.

The remaining rats in both the test and control groups were sacrificed after 8 weeks and the extent of calcification of the implanted tissue determined as above.

The results of the animal study are presented in Table I.

TABLE I

| Porcine cusp tissue | Degree of Calcification | | | |
|---|---|---|---|---|
| | 4 weeks | | 8 weeks | |
| | X-ray[2] | Extraction[1] | X-ray[2] | Extraction[1] |
| SDS-Treated | | | | |
| Rat 1 | 0/6 | 0.0 | 0/6 | 0.37 |
| 2 | 0/6 | 0.0 | 0/6 | 0.45 |
| 3 | 0/6 | 0.0 | 0/6 | 1.21 |
| 4 | 0/6 | 0.0 | 0/6 | 0.20 |
| 5 | 0/6 | 0.0 | 0/6 | 0.39 |
| Control | | | | |
| Rat 1 | 5/6 | 19.07[3] | 6/6 | 2.84 |
| 2 | 6/6 | 4.61 | 6/6 | 12.91 |
| 3 | 6/6 | 5.09 | 6/6 | 4.03 |
| 4 | 5/6 | 10.76 | 6/6 | 6.49 |
| 5 | 4/6 | 8.66 | 6/6 | 3.66 |

[1]Average of 4 values, μg $Ca^{++}$/mg wet wt. tissue
[2]Evaluated by visual examination, 4/6 = 4 of 6 samples evidenced a significant degree of calcification.
[3]Average of 2 values in 4 week data for Control.

As illustrated by the data in Table I, the SDS treatment was effective to substantially inhibit calcification of the porcine valve cusp tissue for a period of 8 weeks under the severe calcification conditions inherent in the rat test. The correlation between calcification in the rat test and human experience is such that the extensive calcification detected in the rat control group after 8 weeks would not be expected to occur in humans until after several years exposure. The SDS treatment would accordingly be expected to retard calcification in humans for an additional period of years beyond that normally experienced prior to the onset of calcification.

The procedure described above is one that has produced good results and constitutes a preferred embodiment of the present invention. The scope of the present invention, however, is not to be limited by the details of the described procedure, and it will be apparent to those skilled in the art that many variations in this procedure are possible. For example, the concentration of the SDS treatment solution may range from about 0.1 to 5.0% or higher, and other water soluble salts of $C_{7-18}$ alkyl sulfates may be substituted for the SDS. Treatment temperatures may range from about 5° C. to 50° C.; and treatment times may range from about 4 hours to several days.

The pH of the treatment solution is preferably from neutral to slightly basic and may range from about 4.0 to 9.0, and most preferably from about 7.0 to 7.5. Buffering agents other than HEPES may be selected according to the desired pH value. In addition, other ingredients both active and inactive may be utilized in combination with the alkyl sulfate in the treatment solution. Such variations may be developed by those skilled in the art with little or no experimentation to suit individual desires.

While the preceding example has also been limited to the treatment of porcine heart valve cusp tissue, the invention is equally applicable to the treatment of veins, arteries, and other tissues taken from pigs, other animals, or humans, all of which are known to be useful for implantation in humans. Human umbilical cords, for example, have been used as arterial grafts after fixation in glutaraldehyde. Similarly, porcine and bovine arteries and veins have also been suggested for use as arterial grafts and A-V fistula grafts. All such tissues are suitable for use in the practice of the present invention.

We claim:

1. A method for inhibiting the mineralization of fixed natural tissue after implantation in a living body comprising contacting fixed natural tissue intended for implantation with an aqueous solution of a water soluble salt of a $C_{7-18}$ alkyl sulfate.

2. The method of claim 1 wherein the aqueous solution is buffered to a pH of 4.0 to 9.0.

3. The method of claim 1 wherein the water soluble salt is selected from the group consisting of sodium, potassium, ammonium and amine salts.

4. The method of claim 1 wherein the $C_{7-18}$ alkyl is a straight chain aliphatic group.

5. The method of claim 1 wherein $C_{7-18}$ alkyl is a branched aliphatic group.

6. The method of claim 1 wherein $C_{7-18}$ alkyl sulfate is selected from the group consisting of lauryl, myristyl, cetyl, steryl and oleyl sulfate.

7. The method of claim 1 wherein said natural tissue is contacted with said salt of $C_{7-18}$ alkyl sulfate for a time sufficient to effectively inhibit future calcification of said tissue after implantation.

8. The method of claim 7 wherein said tissue is contacted with said salt of $C_{7-18}$ alkyl sulfate for a period of at least 4 hours at room temperature.

9. The method of claim 1 wherein the concentration of said salt of $C_{7-18}$ alkyl sulfate in said solution is from about 0.1 to 5% by weight.

10. The method of claim 9 wherein the solution is buffered to a pH of 7.0 to 7.5.

11. A method for inhibiting the calcification of fixed natural tissue after implantation in a living body which comprises contacting fixed tissue intended for implantation with a solution comprising sodium dodecyl sulfate for a time sufficient to effectively inhibit future calcification of said tissue after implantation.

12. The method of claim 11 wherein said solution comprises from about 0.1 to 5% by weight sodium dodecyl sulfate.

13. The method of claim 11 wherein said tissue is contacted with said solution for a time of at least about 4 hours.

14. The method of claim 11 wherein said solution is buffered to a pH of from about 7.0 to 7.5.

15. The method of claim 11 wherein the solution is buffered to a pH of about 7.4 with about 0.005 M N-2-hydroxyethylpiperazine-N'-2-ethanesulfonic acid.

16. The method of claim 15 wherein the concentration of sodium dodecyl sulfate is about 1%.

17. The method of claim 16 wherein the tissue is contacted with said solution of sodium dodecyl sulfate for a period of about 24 hours at ambient temperature.

18. The method of claim 11 wherein the fixed tissue is a glutaraldehyde-fixed porcine heart valve.

19. The method of claim 11 wherein said living body is a human.

* * * * *